US006954047B2

(12) United States Patent
Neubauer

(10) Patent No.: US 6,954,047 B2
(45) Date of Patent: Oct. 11, 2005

(54) TRANSMISSION DETECTOR FOR A WINDOW BODY, IN PARTICULAR THE WINDSHIELD OF A MOTOR VEHICLE, AND A CLEANING DEVICE FOR A VIEWING AREA OF A WINDOW BODY

(75) Inventor: Achim Neubauer, Sinzheim-Vormberg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/398,843

(22) PCT Filed: Jun. 8, 2002

(86) PCT No.: PCT/DE02/02095

§ 371 (c)(1),
(2), (4) Date: Aug. 6, 2003

(87) PCT Pub. No.: WO03/016111

PCT Pub. Date: Feb. 27, 2003

(65) Prior Publication Data

US 2004/0100217 A1 May 27, 2004

(30) Foreign Application Priority Data

Aug. 10, 2001 (DE) ........................................ 101 39 514

(51) Int. Cl.[7] ................................................ H02P 1/04

(52) U.S. Cl. ...................... 318/483; 318/466; 318/467; 250/208.1; 701/36

(58) Field of Search ................................ 318/443, 643, 318/444, DIG. 2; 359/267; 363/494; 382/232; 250/208.1, 574; 315/82, 83, DIG. 15; 356/239.8

(56) References Cited

U.S. PATENT DOCUMENTS 5,453,676 A * 9/1995 Agrotis et al. .............. 318/643
5,796,094 A * 8/1998 Schofield et al. ........ 250/208.1
5,923,027 A * 7/1999 Stam et al. .............. 250/208.1

(Continued)

FOREIGN PATENT DOCUMENTS

| | | | |
|---|---|---|---|
| DE | 38 25 663 | | 2/1989 |
| DE | 044 17 385 | | 11/1995 |
| DE | 197 04 818 | | 8/1997 |
| DE | 298 11 086 | | 10/1998 |
| DE | 198 03 694 | | 4/1999 |
| DE | 197 49 331 | | 5/1999 |
| DE | 198 01 745 | | 7/1999 |
| DE | 198 13 216 | | 9/1999 |
| DE | 199 43 887 | | 3/2000 |
| DE | 199 36 918 | | 4/2000 |
| DE | 198 58 316 | | 6/2000 |
| DE | 199 09 987 | | 9/2000 |
| DE | 198 48 140 | | 4/2001 |
| DE | 199 50 046 | | 4/2001 |
| JP | 9-126998 | * | 5/1997 |
| JP | 2001-141838 | * | 5/2001 |
| JP | 2001-147278 | * | 5/2001 |
| JP | 2001-153969 | * | 6/2001 |
| WO | WO 00/19656 | | 4/2000 |

*Primary Examiner*—Paul Ip
(74) *Attorney, Agent, or Firm*—Kenyon & Kenyon

(57) ABSTRACT

A transmission detector for a window body, in particular the windshield of a motor vehicle, has an optical sensor device which includes an imaging system and a position-sensitive optical detector. In addition, the transmission detector has an analyzing system for the image data recorded by the optical detector. The imaging system is arranged such that sections of a surface of the window body whose distance to one another is comparable to the size of the free aperture of the window body are projected on the optical detector. This allows for a precise allocation of the variables affecting the transmission of the window body. A cleaning system for a viewing area of a window body being equipped with this transmission detector also has a cleaning device which is controlled by the analyzing system. Such a cleaning system may be triggered as needed.

41 Claims, 2 Drawing Sheets

U.S. PATENT DOCUMENTS

| | | | | | |
|---|---|---|---|---|---|
| 6,020,704 | A | * | 2/2000 | Buschur | 318/483 |
| 6,066,933 | A | * | 5/2000 | Ponziana | 318/483 |
| 6,097,023 | A | * | 8/2000 | Schofield et al. | 250/208.1 |
| 6,097,024 | A | * | 8/2000 | Stam et al. | 250/208.1 |
| 6,144,022 | A | * | 11/2000 | Tenenbaum et al. | 250/208.1 |
| 6,207,967 | B1 | * | 3/2001 | Hochstein | 250/574 |
| 6,262,410 | B1 | * | 7/2001 | Stam et al. | 250/208.1 |
| 6,313,454 | B1 | * | 11/2001 | Bos et al. | 250/208.1 |
| 6,320,176 | B1 | * | 11/2001 | Schofield et al. | 250/208.1 |
| 6,323,477 | B1 | * | 11/2001 | Blasing et al. | 250/208.1 |
| 6,353,392 | B1 | * | 3/2002 | Schofield et al. | 340/602 |
| 6,429,933 | B1 | * | 8/2002 | Jackson, Jr. | 356/239.8 |
| 6,495,815 | B1 | * | 12/2002 | Stam et al. | 250/208.1 |
| 6,498,620 | B2 | * | 12/2002 | Schofield et al. | 348/148 |
| 6,555,804 | B1 | * | 4/2003 | Blasing | 250/208.1 |
| 6,559,435 | B2 | * | 5/2003 | Schofield et al. | 250/208.1 |
| 6,580,385 | B1 | * | 6/2003 | Winner et al. | 342/70 |
| 6,614,579 | B2 | * | 9/2003 | Roberts et al. | 359/267 |
| 6,617,564 | B2 | * | 9/2003 | Ockerse et al. | 250/208.1 |
| 6,667,471 | B2 | * | 12/2003 | Bos et al. | 250/208.1 |
| 6,681,163 | B2 | * | 1/2004 | Stam et al. | 701/36 |
| 2002/0167589 | A1 | * | 11/2002 | Schofield et al. | 348/148 |
| 2003/0069674 | A1 | * | 4/2003 | Stam et al. | 701/36 |
| 2003/0122930 | A1 | * | 7/2003 | Schofield et al. | 348/148 |
| 2003/0201380 | A1 | * | 10/2003 | Ockerse et al. | 250/208.1 |

* cited by examiner

TRANSMISSION DETECTOR FOR A WINDOW BODY, IN PARTICULAR THE WINDSHIELD OF A MOTOR VEHICLE, AND A CLEANING DEVICE FOR A VIEWING AREA OF A WINDOW BODY

FIELD OF THE INVENTION

The present invention relates to a transmission detector for a window body, in particular the windshield of a motor vehicle, and a cleaning device for a viewing area of a window body.

BACKGROUND INFORMATION

A transmission detector for a window body, and a cleaning device for a viewing area of the window body are referred to in German Patent Application No. 197 49 331. A sensor array, situated on the base of an interior mirror of a motor vehicle, parallel to the exterior surface of its windshield, operates there as a position-sensitive optical detector for detecting objects, e.g., rain droplets on the exterior of the windshield. The sensor array covers only a small section of the windshield. Influencing factors on the transmission of the windshield which do not evenly affect the entire windshield surface may thus be detected either with relatively great uncertainty or not at all.

Another transmission detector and a cleaning device equipped with it are referred to in German Patent Application No. 199 43 887. Here, the radiation, emitted from a relatively small section of a windshield of a motor vehicle, is utilized with the aid of a position-insensitive detector for transmission detection. In addition to the disadvantages mentioned, due to the coverage of only a small section of the window body, additional limits may arise here due to the fact that, by using such a transmission detector, it cannot be determined which type of effect, e.g., which type of object on the windshield, has triggered the transmission change of the window body.

SUMMARY OF THE INVENTION

An object of an exemplary embodiment the present invention is to refine a transmission detector so that transmission effects which are unevenly spread across the window body may also be reliably detected.

By detecting sections of the surface of the window body, which are distanced from one another by an amount on the order of magnitude of the free aperture, it may be determined, by using the transmission detector according to the present invention, whether or not a transmission effect, acting evenly on the window body, exists. If an even transmission effect exists, e.g., due to rain droplets or an even dust or pollen layer on the window body, then the sections that are distanced from one another are affected in the same way. This is not believed to be the case when an uneven transmission effect exists, e.g., an uneven soiling of the window body. Where applicable, the transmission detector may be part of an optical detection device, e.g., for the identification of driving lanes, resulting in improved cost efficiency due to the joint utilization of components.

An exemplary sensor array in the position-sensitive optical detector may have a high positional resolution. This is intended to improve the precision of the transmission detector in determining the type of transmission effect of the window body.

An exemplary CCD ("charge coupled device") array of the sensor array is intended to be highly light-sensitive and may be in a compact design.

Sections of the surface of the window body which are farther distanced from one another may also be imaged with little optical effort by using a wide-angle lens in the imaging system. If increased requirements must be taken into account, e.g., due to the shape of the window body or to the condition that the entire surface of the window body must be imaged if possible, an imaging system having a plurality of optical components may be used.

By using an aperture in the optical sensor device, the area of the window body detected by the transmission detector may be adapted so that, for example, a predefined transmission measuring program for determining the transmission effect may be run. In addition, a standard transmission detector may be adapted to a plurality of differently dimensioned window bodies. Exposure control of the optical sensor device may also be implemented by using an aperture.

A controllable aperture opening controlled by an actuator may at least better ensure an automated selection of the sections of the surface of the window body to be imaged.

By using an actuator that communicates with the analyzing system via a signal link, an area of the surface of the window body to be imaged may be selected as a function of an analysis result of the transmission detector. More complicated transmission measuring programs may also be implemented in an automated fashion, in which an additional area or several additional areas are selected and measured as a function of the analysis result of the transmission measurement of a certain area. This may take place on the basis of the initially measured area if, for example, the type and the distribution of objects on the window body, affecting the transmission, are only known inaccurately or not yet at all.

A plurality of apertures in the optical sensor device may also facilitate the selection of complicated, i.e., irregularly shaped, sections of the surface of the window body to be imaged.

A radiation source of the optical sensor device, for illuminating the sections to be imaged, allows transmission detection even when no daylight or other external light is available.

IR radiation emitted by the radiation source may be perceived as undisturbing to the user. Moreover, current optical detectors are particularly sensitive in certain IR wavelength ranges.

Blurred imaged sections of the surface of the window body may also be analyzed by using analyzing systems involving a contrast, Fourier or auto-correlation analysis of the intensity distribution of the imaged sections that is performed based on the image data recorded by the optical detector. The dependency of the contrast, the Fourier components and/or the auto-correlation function on further defined parameters accessible to the measurement offer a measured variable which makes an adequately precise conclusion on the type of transmission effect possible.

A comparator for comparing the analyzed image data with reference value makes a relatively inexpensive analysis of the optical image data possible.

A refinement in determining the transmission effect is achievable by using the comparator in which the reference values are dynamically adjusted to the results of a plurality of sets of analyzed image data.

A neural network in the comparator may be particularly suitable for implementing a comparator including dynamic adjustment of the reference values.

Another object of the exemplary embodiment of the present invention is to provide a cleaning device of the type mentioned earlier, in which the improved possibilities of detecting a transmission effect by using the transmission detector are utilized.

This object may be achieved according to an exemplary embodiment of the present invention by using a cleaning system controlled by the analyzing system having a transmission detector.

The cleaning device in such a cleaning system is only to be activated if this is actually necessary due to transmission effects on the window body which are removable by cleaning. This improves the efficiency of the cleaning system.

A window wiper body, including a window wiper body, is a cleaning instrument that is inexpensive and sufficient in its cleaning effect.

A window washing device of the cleaning device results in an improved cleaning effect.

In a cleaning system, in which the imaged sections lie in a user's field of vision through the window body, the transmission detection takes place where the removal of disturbing transmission effects is most important to the user.

Disturbing transmission effects, which are not detected, are essentially eliminated by using a cleaning system in which the imaged sections cover the field of vision.

The danger of false activation of the cleaning device may be minimized by controlling the cleaning device with the analyzing system only after a first time activation by the user.

DETAILED DESCRIPTION

Figure 1:
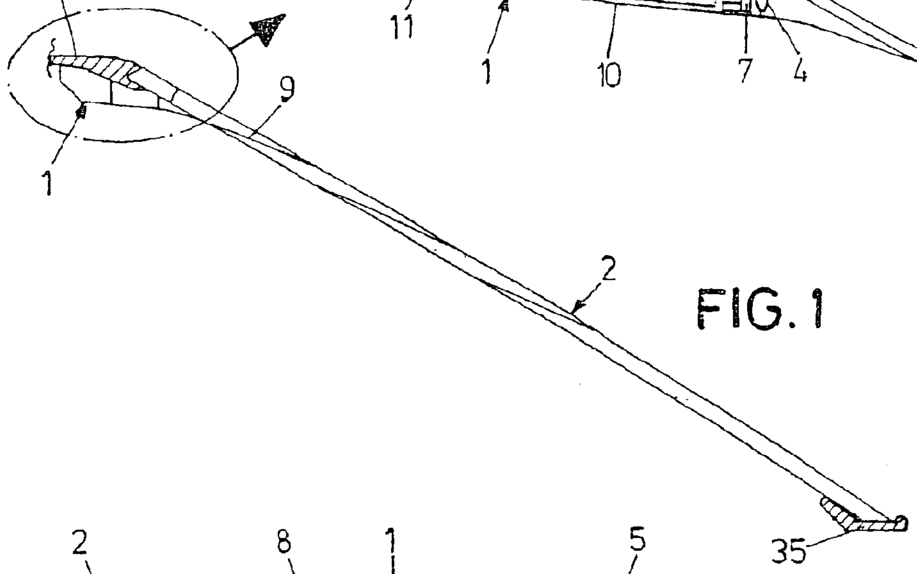
FIG. 1 shows a vertical section through a passenger car in the area of a windshield, parallel to the longitudinal axis of the passenger car.

A transmission detector, referenced in the drawing with number 1, is used for detecting foreign substances on a windshield 2 of a passenger car, e.g., rain droplets, dust particles, pollen, or local soiling such as insect residues. Transmission detector 1 is part of a cleaning system for windshield 2. Windshield 2 is depicted in FIG. 1 in a vertical section along the longitudinal axis of the passenger car between roof 3 of the passenger car and a body area 35 connected to the lower area of windshield 2.

Transmission detector 1 is mounted in a housing and situated on the roof liner of the passenger car in the transition area between the upper end area of windshield 2 and roof 3 of the passenger car.

Figure 3:
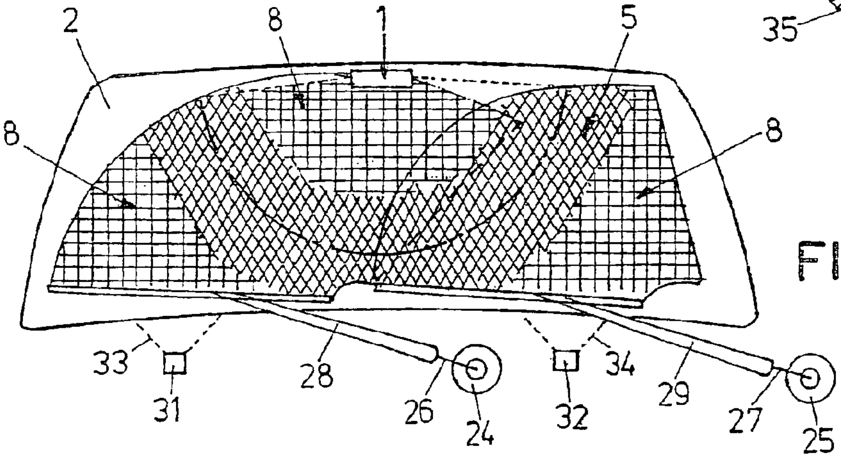
FIG. 3 shows a frontal view of the windshield of a passenger car including a cleaning system having cleaning devices for the windshield.

Transmission detector 1 covers the outside surface of windshield 2, with the help of a wide-angle lens 4. As a function of the depth of field of wide-angle lens 4, since windshield 2 is inclined toward the optical axis of wide-angle lens 4, the entire external surface of windshield 2 is not imaged but an image section 5 in the form of a strip shaped as a semicircle is sharply projected on the photosensitive screen of a video array 6. A CCD array may be used as video array 6. In FIG. 3, showing a view of the passenger car in the area of windshield 2 from the front, image section 5 is highlighted by a rhomboidal hatch. Reference sections 8 of the external surface of windshield 2 which are also detectable by transmission detector 1 are depicted by a quadratic hatch in FIG. 3. The overall area of windshield 2, detectable by video array 6, which is composed of image section 5 and reference sections 8 covers a surface area of windshield 2 which is comparable to the entire field of vision, i.e., the free aperture, of windshield 2.

In order to meet increased imaging requirements, an imaging system may also be utilized as an alternative to a wide-angle lens 4.

Figure 2:
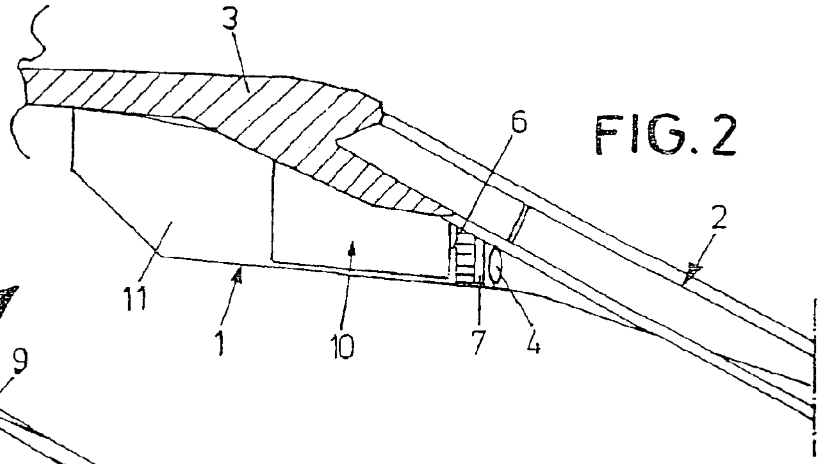
FIG. 2 shows an enlarged detail from FIG. 1.

An aperture 7 is arranged to select the section of windshield 2 to be detected by video array 6, and is situated in the imaging beam path (imaging beams 9, see FIGS. 1 and 2) between wide-angle lens 4 and video array 6. The opening of aperture 7 may be preset by the manufacturer or may be readjusted during operation of transmission detector 1 by using an actuator (not shown, see FIG. 5).

A device for decoupling imaging beams 9 from windshield 2 may be inserted between wide-angle lens 4 and the imaging system.

Video array 6 communicates via signals with analyzing system 10 having an integrated control unit 11 which controls the cleaning components for windshield 2 yet to be described.

Figure 5:
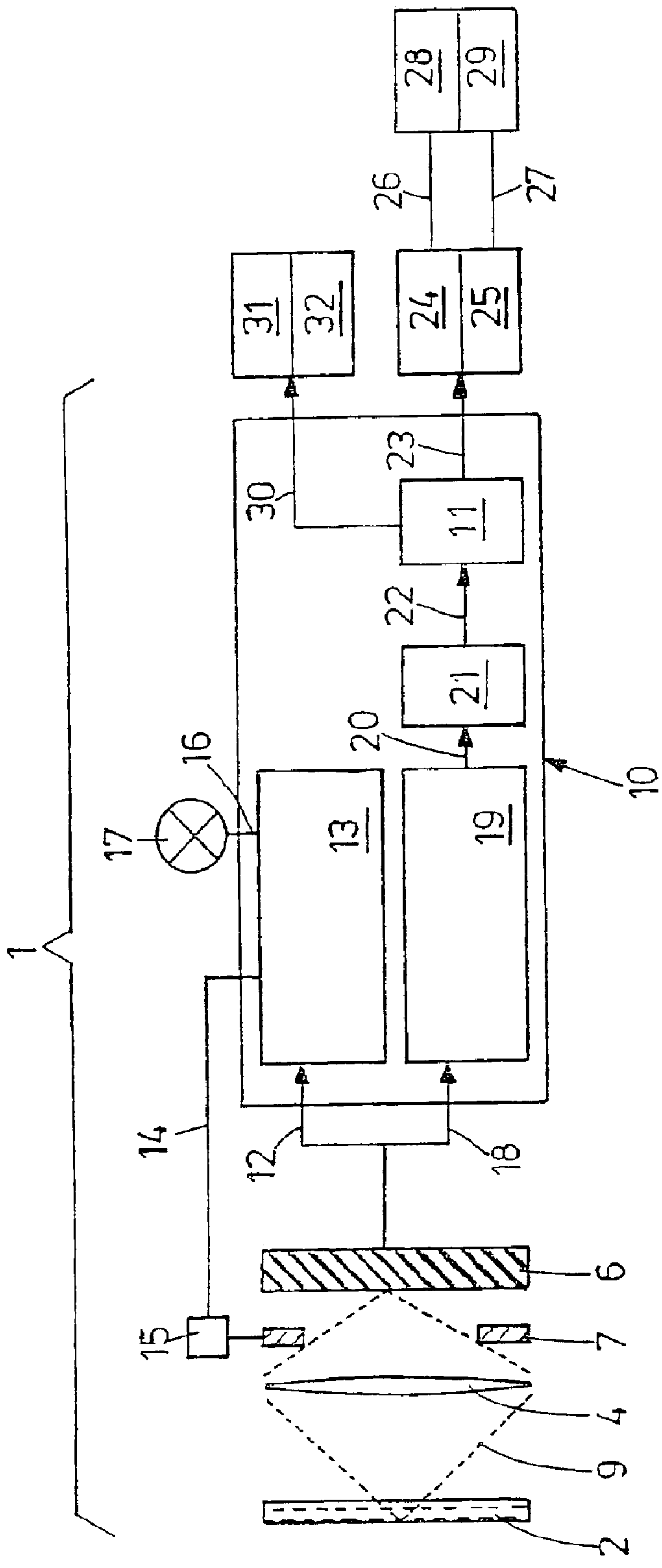
FIG. 5 shows a schematic block diagram of the cleaning system.

The internal design of analyzing system 10 is shown in the block diagram of FIG. 5, which schematically illustrates the optical components of transmission detector 1.

Video array 6 communicates with an exposure controller 13 of analyzing system 10 via data line 12. The analyzing system is connected to an actuator 15, which is coupled to aperture 7 via a control lead 14. Furthermore, exposure controller 13 is connected to an IR transmitter via a control lead 16.

Video array 6 is connected to an analyzing device 19 of analyzing system 10 via an additional data line 18. The analyzing device communicates via a data line 20 with a comparator 21 which in turn communicates with control unit 11 of analyzing system 10 via a signal line 22.

Control unit 11 is connected to two windshield wiper motors 24, 25 (see FIG. 3) via a control lead 23, the motors being coupled with wiper arms 28, 29 either via rods 26, 27 or directly via the outputs of the windshield wiper motors.

Control unit 11 of analyzing system 10 is connected to two windshield washer units 31, 32 (see FIG. 3) for windshield 2 via a control lead 30. Spray areas 33, 34 of windshield washer units 31, 32 are indicated in FIG. 3 with dashed lines.

Figure 4:
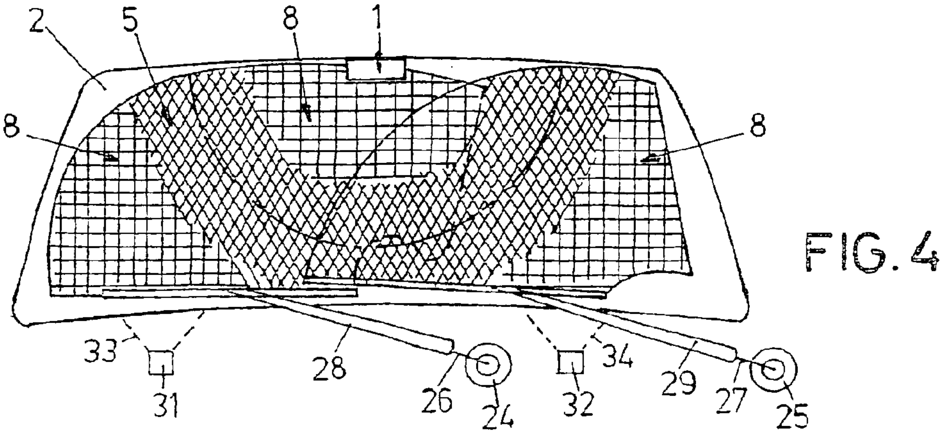
FIG. 4 shows another frontal view of the windshield of a passenger car including a cleaning system having cleaning devices for the windshield.

FIGS. 3 and 4 show two alternative exemplary embodiments of cleaning systems for windshield 2 which differ in the areas of the external surface of windshield 2 reached by wiper arms 28, 29.

The same components which have been explained with reference to FIG. 3 are labeled with the same reference numbers in FIG. 4 and are not discussed again in greater detail.

In the wiper configuration according to FIG. 4, wiper arms 28, 29 reach a larger area of windshield 2 than is the case in the wiper configuration according to FIG. 3. Reference sections 8, detected by transmission detector 1, are also similarly enlarged.

The cleaning system works as follows:

Via aperture 7 and wide-angle lens 4, video array 6 records image section 5 and reference sections 8 as a function of the opening of aperture 7. Objects on windshield 2 are sharply imaged within image section 5, while objects in reference sections 8 are detected in a blurred form by video array 6. The sharply imaged objects are detected with the aid of an analysis of the measured intensity distribution which is yet to be described. The objects, which lie outside the depth of field area of image section 5, i.e., in reference sections 8, are likewise detected based upon the measured intensity distribution by measuring the blur of imaged contours. This blur depends on whether windshield 2 is affected in its transmission by, e.g., rain droplets (defocusing) or by ice or dust (dispersion).

The presence of such interfering objects appears in image section 5 through sharply displayed details in the image, i.e., in an intensity variation over relatively small image sections. In many cases, the type of intensity variation is intrinsic for the type of soiling. Therefore, the type of soiling may be identified by a comparison with reference dispersions yet to be described.

The image data recorded by video array 6 are initially transmitted to exposure controller 13 via data line 12. Based upon a comparison with an exposure setpoint value, it is determined there whether the illumination of windshield 2 is sufficient for transmission detection, and whether a section specification for the section of windshield 2 to be detected is fulfilled.

If the exposure setpoint value is not met, then IR transmitter 17, which illuminates windshield 2 for transmission detection, is switched on via control lead 16. If the section specification for the section of windshield 2 to be detected is not fulfilled, then actuator 15 is triggered via control lead 14 and the section specification for the section of windshield 2 to be detected is adjusted via the opening of aperture 7.

When it is ensured that the setpoint specifications discussed have been met, then the image data recorded by video array 6 is transmitted to analyzing device 19 via data line 18. The analysis of the intensity distribution detected is then performed by analyzing device 19 in cooperation with comparator 21. A number of methods from digital image processing are available for performing this analysis. One method which is based upon the analysis of a contrast spectrum is described as an example, as follows.

A multi-scale analysis for receiving the contrast spectrum is initially performed, in which the recorded image is decomposed into several images having decreasing resolution by repeated use of a smoothing operation. A global contrast measurement is calculated at each resolution level, e.g., the standard deviation of the intensity values detected. The contrast measure, plotted against the resolution, forms the contrast spectrum of the image recorded by video array 6. If windshield 2 is scratch-free and free of objects, only blurred objects from farther away are imaged. Thus contrasts appear in the contrast spectrum only at low resolutions.

If, however, there are objects in image section 5 of windshield 2, then fine details are also imaged. In this case there are also contrasts in the contrast spectrum at higher resolutions. The fact that, contrary to sharp images, the contrast in blurred images declines more steeply with increasing resolution than in sharp images, is utilized for blurred reference sections 8, since fine details are more affected by blurred imaging than rough image features. The downward slope of the contrast spectrum over the resolution is therefore a measurement for the blurriness of the image.

The contrast spectrum determined in analyzing device 19 is transmitted to comparator 21 via lead 20 and is compared there with stored reference contrast spectra. Different types of visual obstruction are distinguished here based upon their similarity to certain reference distributions. An even dust layer typically having the same granular size results in an isolated peak in the contrast spectrum, while rain droplets which differ in size show a wider contrast distribution.

Based upon the result of the comparison in comparator 21, the latter either controls windshield wiper motors 24, 25 via control lead 23 or it controls windshield washer units 31, 32 via control lead 30 when such visually obstructing objects are present.

If rain droplets are identified by the comparison in comparator 21, then only windshield wiper motors 24, 25 are triggered for example. If the presence of a dust or pollen layer on windshield 2 is identified, then both windshield washer units 31, 32 and windshield wiper motors 24, 25 are activated. If local soiling is present, then the activation of only one windshield wiper motor 24 or 25 and/or one windshield washer unit 31 or 32 is possibly sufficient. Depending on the type of visual obstruction on the window, i.e., type, distribution, and intensity of soiling, rain intensity, rain droplet frequency, etc., one or both windshield wiper motors may be operated or triggered using different wiping speeds. If icing on the windshield is identified it may be advisable, in particular in a parked vehicle, to initially only activate the washer unit in order to remove the ice using the antifreeze in the windshield washer water. During defrosting of the ice layer and the corresponding transmission change, the windshield wiper motors may then be activated. This control method contributes to the protection of the wiper blades.

The reference contrast spectra and reference distributions may be obtained from images of video array 6 which were recorded immediately after a wiper or washer operation. Using these reference distributions, a decision may be made about initializing a subsequent wiper or washer operation.

Alternatively to contrast measuring, a measure of the intensity variation of the image recorded by video array 6 may also be determined using other reference variables.

An example of such a reference variable is an auto-correlation function over the pixel distance of video array 6. Since only background objects are displayed, all displayed objects appear highly blurred at unobstructed view, i.e., the auto-correlation function of the image drops only slowly over the distance. If, however, there are objects on the windshield then the image varies on much smaller distances so that its auto-correlation function drops much faster.

A reference variable may also be at least a two-dimensional Fourier transform. In the Fourier spectrum (amplitude over the spatial frequency) a blurred image appears due to the fact that the amplitude of the high spatial frequencies, which represent the finer image details, is highly attenuated compared to a sharp image.

Finally, an indirect classification approach may be provided in which the reference variables are generated by an appropriate analyzing device, e.g., a polynomial classifier or a neural network, by presenting a large number of exemplary images or a plurality of sets of analyzed image data, the analyzing device being trained to differentiate between sharp images of objects and images with blurred objects by analyzing the classification results.

Instead of an aperture 7, a plurality of apertures may also be utilized with which it is possible to finely adjust the area of windshield 2 to be detected by video array 6.

Control unit 11 may be designed such that windshield wiper motors 24, 25 and windshield washer units 31, 32 may only be triggered by comparator 21 if windshield wiper motors 24, 25 and windshield washer units 31, 32 have been first manually triggered by the user. This prevents an erroneous initial operation in the event of wrong detection. Windshield wiper motors 24, 25, and windshield washer units 31, 32 may also be triggered as a function of the driver seat occupancy or the operational status of the vehicle (vehicle is parked/ engine idles/ vehicle moves).

What is claimed is:

1. A transmission detector for a windshield window body, comprising:

an optical sensor device, including an imaging system having a wide-angle lens, a position-sensitive optical detector and an aperture; and an analyzing system for analyzing image data recorded by the optical detector, wherein sections of a surface of the windshield window body, covering approximately an entire span of the windshield window body, are projected on the optical detector.

2. The transmission detector of claim 1, wherein the position-sensitive optical detector includes a sensor array.

3. The transmission detector of claim 2, wherein the sensor array includes a CCD array.

4. The transmission detector of claim 1, wherein the optical sensor device includes at least one aperture via selected ones of the sections to be imaged.

5. The transmission detector of claim 4, further comprising: at least one actuator for controlling the at least one aperture opening.

6. The transmission detector of claim 5, wherein the at least one actuator communicates with the analyzing system via a signal link.

7. The transmission detector of claim 1, wherein the optical sensor device includes apertures.

8. The transmission detector of claim 1, wherein the optical sensor device includes a radiation source for illuminating the sections to be imaged.

9. The transmission detector of claim 8, wherein the radiation source is operable to emit IR radiation.

10. The transmission detector of claim 1, wherein the analyzing system is operable to perform a contrast analysis of an intensity distribution of the imaged sections based upon image data recorded by the optical detector.

11. The transmission detector of claim 1, wherein the analyzing system is operable to perform a Fourier analysis of an intensity distribution of imaged sections based upon image data recorded by the optical detector.

12. The transmission detector of claim 1, wherein the analyzing system is operable to perform an auto-correlation analysis of an intensity distribution of imaged sections based upon the image data recorded by the optical detector.

13. The transmission detector of claim 1, further comprising: a comparator for comparing analyzed image data with reference values.

14. The transmission detector of claim 13, wherein the reference values are dynamically adjusted to the results of a plurality of sets of analyzed image data.

15. The transmission detector of claim 14, wherein the comparator includes a neural network.

16. The transmission detector of claim 1, wherein the windshield window body is a windshield of a motor vehicle.

17. A cleaning system for a field of vision of a windshield window body, comprising:

a transmission detector, including an optical sensor device having an imaging system including a wide angle lens, a position-sensitive optical detector and an aperture, and including an analyzing system for analyzing image data recorded by the optical detector, wherein sections of a surface of the windshield window body, having an area covering approximately an entire span of the windshield window body, are projected on the optical detector, and a cleaning device controlled by the analyzing system.

18. The cleaning system of claim 17, wherein the cleaning device includes a window wiper body.

19. The cleaning system of claim 17, wherein the cleaning device includes a window washing device.

20. The cleaning system of claim 17, wherein the imaged sections lie in a user's field of vision through the windshield window body.

21. The cleaning system of claim 20, wherein the imaged sections essentially cover the field of vision.

22. The cleaning system of claims 17, wherein the analyzing system controls the cleaning device only after a first time activation by the user.

23. A transmission detector for a windshield window body, comprising:

an optical sensor device, including an imaging system having a wide-angle lens, a position-sensitive optical detector and at least one aperture;

an analyzing system for analyzing image data recorded by the optical detector, wherein sections of a surface of the windshield window body, having an area that approximately covers an entire span of the windshield window body, are projected on the optical detector; and at least one actuator for controlling the at least one aperture opening.

24. The transmission detector of claim 23, wherein the position-sensitive optical detector includes a sensor array.

25. The transmission detector of claim 24, wherein the sensor array includes a CCD array.

26. The transmission detector of claim 23, wherein the at least one actuator communicates with the analyzing system via a signal link.

27. The transmission detector of claim 23, wherein the optical sensor device includes a radiation source for illuminating the sections to be imaged.

28. The transmission detector of claim 27, wherein the radiation source is operable to emit IR radiation.

29. The transmission detector of claim 23, wherein the analyzing system is operable to perform a contrast analysis of an intensity distribution of the imaged sections based upon image data recorded by the optical detector.

30. The transmission detector of claim 23, wherein the analyzing system is operable to perform a Fourier analysis of an intensity distribution of imaged sections based upon image data recorded by the optical detector.

31. The transmission detector of claim 23, wherein the analyzing system is operable to perform an auto-correlation analysis of an intensity distribution of imaged sections based upon the image data recorded by the optical detector.

32. The transmission detector of claim 23, further comprising: a comparator for comparing analyzed image data with reference values.

33. The transmission detector of claim 32, wherein the reference values are dynamically adjusted to the results of a plurality of sets of analyzed image data.

34. The transmission detector of claim 33, wherein the comparator includes a neural network.

35. A cleaning system for a field of vision of a windshield window body, comprising:

a transmission detector for a window body, including:

an optical sensor device, including an imaging system having a wide-angle lens, a position-sensitive optical detector and at least one aperture an analyzing system for analyzing image data recorded by the optical detector, wherein sections of a surface of the windshield window body, having an area that approximately covers an entire span of the windshield window body, are projected on the optical detector; and at least one actuator for controlling the at least one aperture opening; and a cleaning device controlled by the analyzing system.

36. The cleaning system of claim 35, wherein the cleaning device includes a window wiper body.

37. The cleaning system of claim 35, wherein the cleaning device includes a window washing device.

38. The cleaning system of claims 35, wherein the imaged sections lie in a user's field of vision through the windshield window body.

39. The cleaning system of claim 35, wherein the imaged sections essentially cover the field of vision.

40. The cleaning system of claims 35, wherein the analyzing system controls the cleaning device only after a first time activation by the user.

41. The transmission detector of claim 35, wherein the windshield window body is a windshield of a motor vehicle.

* * * * *